US010264968B2

(12) United States Patent
Gross

(10) Patent No.: US 10,264,968 B2
(45) Date of Patent: Apr. 23, 2019

(54) BODY WORN SENSORS NETWORK WITH REDUNDANT PARAMETER PRIORITIZATION AND TEMPORAL ALIGNMENT

(75) Inventor: Brian David Gross, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1327 days.

(21) Appl. No.: 13/825,978

(22) PCT Filed: Sep. 21, 2011

(86) PCT No.: PCT/IB2011/054132
§ 371 (c)(1),
(2), (4) Date: May 14, 2013

(87) PCT Pub. No.: WO2012/042437
PCT Pub. Date: Apr. 5, 2012

(65) Prior Publication Data
US 2013/0237775 A1 Sep. 12, 2013

Related U.S. Application Data

(60) Provisional application No. 61/388,024, filed on Sep. 30, 2010.

(51) Int. Cl.
A61B 5/00 (2006.01)
A61B 5/0205 (2006.01)
(Continued)

(52) U.S. Cl.
CPC .......... A61B 5/0002 (2013.01); A61B 5/0205 (2013.01); A61B 5/7221 (2013.01);
(Continued)

(58) Field of Classification Search
CPC ... A61B 5/0002; A61B 5/0205; A61B 5/7221; A61B 5/746; A61B 5/00; G06F 19/3406; G06F 19/3418; G06F 19/345; G06F 19/30
(Continued)

(56) References Cited

U.S. PATENT DOCUMENTS 8,493,993 B2 7/2013 Patel et al.
8,834,020 B2 9/2014 Abreu
(Continued)

FOREIGN PATENT DOCUMENTS

JP 2006247386 9/2006
WO 2007050487 5/2007
(Continued)

OTHER PUBLICATIONS

Otto, C., et al.; System Architecture of a Wireless Body Area Sensor Network for Ubiquitous Health Monitoring; 2006; Journal of Mobile Multimedia; 1(4)307-326.
(Continued)

Primary Examiner — Carl H Layno
Assistant Examiner — Dacheng Xie

(57) ABSTRACT

Each sensor of a plurality of sensors operates independently to perform at least a monitoring function acquiring sensor data indicative of a common physiological parameter and a grading function performed occasionally to assign a current signal quality grade for the sensor that is indicative of operational status of the monitoring function of the sensor. A data structure stores information pertaining to the plurality of sensors including at least priorities of the plurality of sensors respective to the common physiological parameter and the current signal quality grades for the sensors. Each sensor further operates to perform at least one output function generating an output signal conditional upon content of
(Continued)

Figure 1:
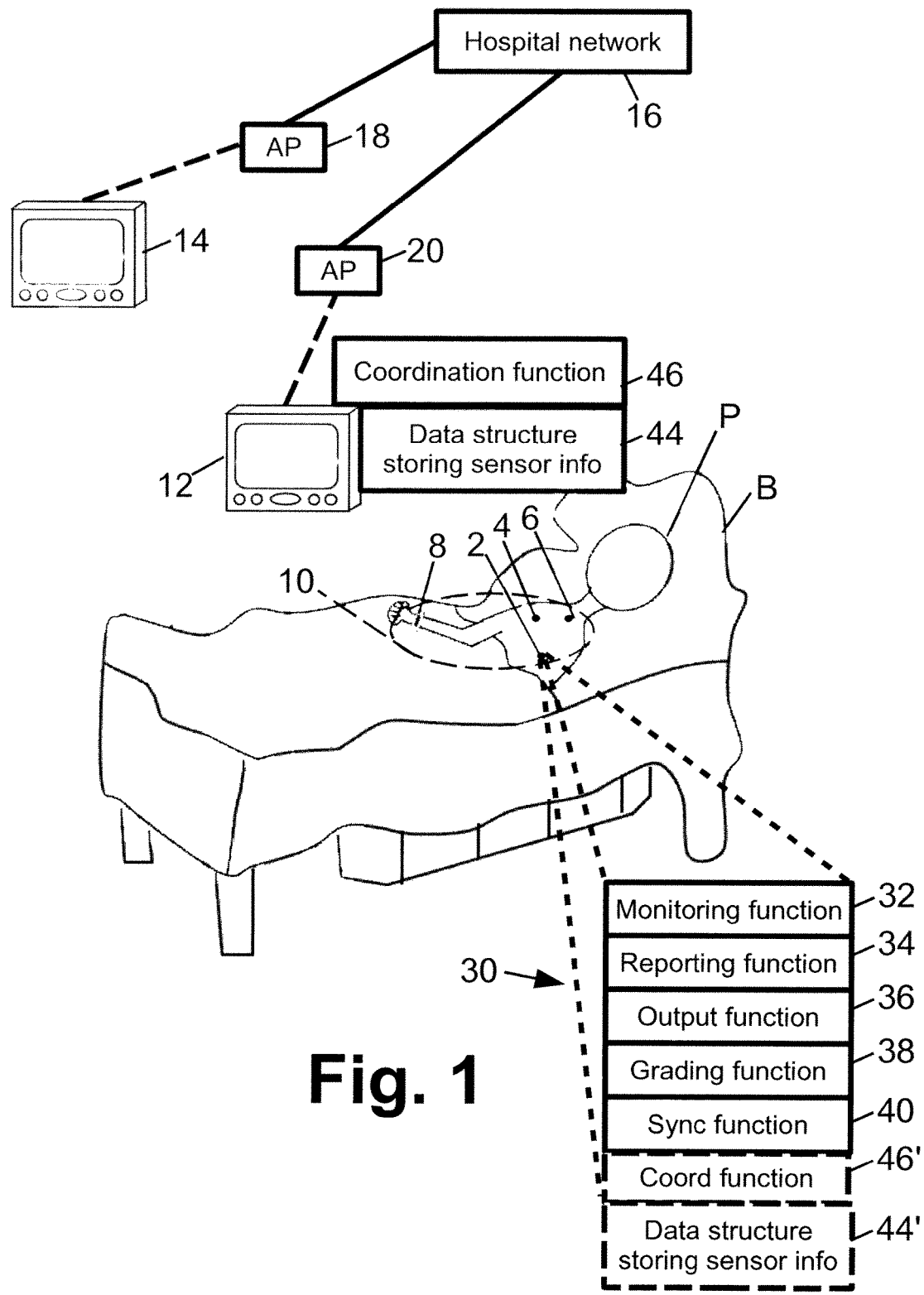

the data structure including at least the priorities and the current signal quality grades of the sensors indicating the output function should be performed.

17 Claims, 5 Drawing Sheets

(51) Int. Cl.
G06F 19/00 (2018.01)
G16H 40/63 (2018.01)
G16H 50/20 (2018.01)

(52) U.S. Cl.
CPC ......... *G06F 19/3418* (2013.01); *G16H 40/63* (2018.01); *G16H 50/20* (2018.01); *A61B 5/746* (2013.01)

(58) Field of Classification Search
USPC .................................................. 600/300–301
See application file for complete search history.

(56) References Cited

U.S. PATENT DOCUMENTS

| | | |
|---|---|---|
| 2005/0119833 A1 | 6/2005 | Nanikashvili |
| 2007/0299480 A1 | 12/2007 | Hill |
| 2008/0097553 A1* | 4/2008 | John ................. A61B 5/4809 607/60 |
| 2008/0228045 A1* | 9/2008 | Gao .................. A61B 5/0024 600/301 |
| 2009/0069642 A1 | 3/2009 | Gao et al. |
| 2009/0105605 A1* | 4/2009 | Abreu ............... A61B 5/0008 600/549 |
| 2009/0135886 A1 | 5/2009 | Robertson et al. |
| 2010/0101022 A1* | 4/2010 | Riley ................ A61B 5/0816 5/600 |
| 2010/0240982 A1* | 9/2010 | Westbrook ......... A61B 5/087 600/391 |

FOREIGN PATENT DOCUMENTS

| | | |
|---|---|---|
| WO | 2009033374 A1 | 3/2009 |
| WO | 2009138521 A1 | 11/2009 |

OTHER PUBLICATIONS

Romer, K.; Time Synchronization and Localization in Sensor Networks; 2005; Dissertation ETH No. 10106; Submitted to the Swiss Federal Institute of Technology, Zurich.

Shnayder, V., et al.; Sensor Networks for Medical Care; 2005; Technical Report TR-08-05; Division of Engineering and Applied Sciences, Harvard University.

\* cited by examiner

| Sensor | Latency time | Priority | Current grade | Output ? |
| --- | --- | --- | --- | --- |
| HR | 0 msec | 1 | Pass | Yes |
| ECG | 35 msec | 3 | Pass | No |
| Oximeter | 7.0 msec | 7 | Pass | No |

Fig. 4

| Sensor | Latency time | Priority | Current grade | Output ? |
| --- | --- | --- | --- | --- |
| HR | 0 msec | 1 | Fail | No |
| ECG | 35 msec | 3 | Pass | Yes |
| Oximeter | 7.0 msec | 7 | Pass | No |

Fig. 5

| Sensor | Latency time | Priority | Current grade | Output ? |
| --- | --- | --- | --- | --- |
| HR | 0 msec | 1 | Fail | Yes |
| ECG | 35 msec | 3 | Fail | Yes |
| Oximeter | 7.0 msec | 7 | Fail | Yes |

Fig. 6

BODY WORN SENSORS NETWORK WITH REDUNDANT PARAMETER PRIORITIZATION AND TEMPORAL ALIGNMENT

CROSS REFERENCE TO RELATED APPLICATIONS

This application is a national filing of PCT application Serial No. PCT/IB2011/054132, filed Sep. 21, 2011, published as WO 2012/042437 A2 on Apr. 5, 2012, which claims the benefit of U.S. provisional application Ser. No. 61/388,024 filed Sep. 30, 2010, which is incorporated herein by reference.

The following relates to the medical monitoring arts and related arts.

Medical monitoring by sensors such as electrocardiographic (ECG) sensors, blood oxygenation ($SpO_2$) sensors, blood pressure (BP) sensors, respiration sensors, core body temperature sensors, activity sensors or so forth provide real-time vital sign data that can detect abnormal medical events, and serves as an early warning system to detect potentially life-threatening medical conditions. Early intervention in response to audible and/or visual alarms output by such sensors saves lives. Indeed, patients are sometimes monitored by a number of different vital sign sensors, providing an advantageous degree of redundancy of certain parameters in case one sensor becomes noisy or fails. In some cases surrogates to primary physiological signals can be obtained from another sensor technology (for example, pulse from electrocardiograph, or photoplethismogram, or accelerometer, or so forth).

However, false alarms are a substantial problem with vital sign sensors. In a typical scenario, a false alarm indicating a patient is in cardiac arrest potentially causes an emergency response by a team of medical personnel. False alarms take medical personnel away from other critical duties, increasing stress on medical personnel and patients, and can desensitize medical personnel to the emergency alarm which can in turn lead to delayed response to real emergency alarms or even to medical personnel ignoring a real emergency alarm under the assumption that it is a false alarm. A false alarm can also potentially create an immediately life-threatening situation if the false alarm occurs at the same time that another patient experiences a real cardiac arrest event, so as to interfere with and/or delay response to the real cardiac arrest event. The likelihood of false alarms is increased for patients who are monitored by multiple vital sign sensors, since any one of these sensors has the potential to output a false alarm, either due to a sensor malfunction or due to a loss of operative connection between the sensor and the patient (for example, an ECG lead may become detached due to patient motion thereby causing the ECG sensor to generate a false alarm).

The following provides new and improved apparatuses and methods as disclosed herein.

In accordance with one disclosed aspect, a system comprises: a plurality of sensors, each sensor of the plurality of sensors operating independently of the other sensor or sensors of the plurality of sensors to perform at least a monitoring function acquiring sensor data indicative of a common physiological parameter and a signal quality grading function performed occasionally to assign a current signal quality grade for the sensor wherein the current grade is indicative of operational status of the monitoring function of the sensor; and a data structure storing information pertaining to the plurality of sensors including at least priorities of the plurality of sensors respective to the common physiological parameter and the current signal quality grades for the sensors of the plurality of sensors. Each sensor of the plurality of sensors further operates to perform at least one output function generating an output signal conditional upon content of the data structure including at least the priorities and the current signal quality grades of the sensors of the plurality of sensors indicating the output function should be performed.

In accordance with another disclosed aspect, a method comprises: generating a plurality of sensor data streams each indicative of a common physiological parameter; assigning a current signal quality grade for each sensor data stream assessing current reliability of that sensor data stream; selecting an output sensor data stream from the plurality of sensor data streams based on time invariant sensor data stream priorities and the current signal quality grades; and generating an output based on the selected output sensor data stream.

In accordance with another disclosed aspect, an apparatus comprises a sensor configured to perform a monitoring function acquiring sensor data indicative of a common physiological parameter, and a grading function assigning a current grade for the sensor that is indicative of operational status of the monitoring function of the sensor and conveying the current grade to at least one device other than the sensor.

In accordance with another disclosed aspect, an apparatus comprises a set of sensors capable of self-aligning with each other's continuous sensor signal with regards to temporal alignment of physiologic data stream.

In accordance with another disclosed aspect, an apparatus comprises a set of sensors capable of determining their own data reliability or physiologic signal quality based on signal comparisons with temporally aligned data streams of other measurements.

In accordance with another disclosed aspect, an apparatus comprises a set of sensors capable of adaptive and self resolving master-slave time relationships based on each sensors signal quality and absolute ranking of sensor's method of acquiring physio logic data.

One advantage resides in reduced likelihood of generating false alarms.

Another advantage resides in reduced likelihood of generating false alarms while retaining the substantial benefits of redundant monitoring of a common physiological parameter by a plurality of independently operating sensors or a plurality of independent sensor data streams.

Another advantage resides in providing time-synchronized sensor data streams indicative of a common physiological parameter.

Further advantages will be apparent to those of ordinary skill in the art upon reading and understanding the following detailed description.

FIG. 1 diagrammatically shows a system including a plurality of sensors operating in accordance with approaches disclosed herein.

Figure 2:
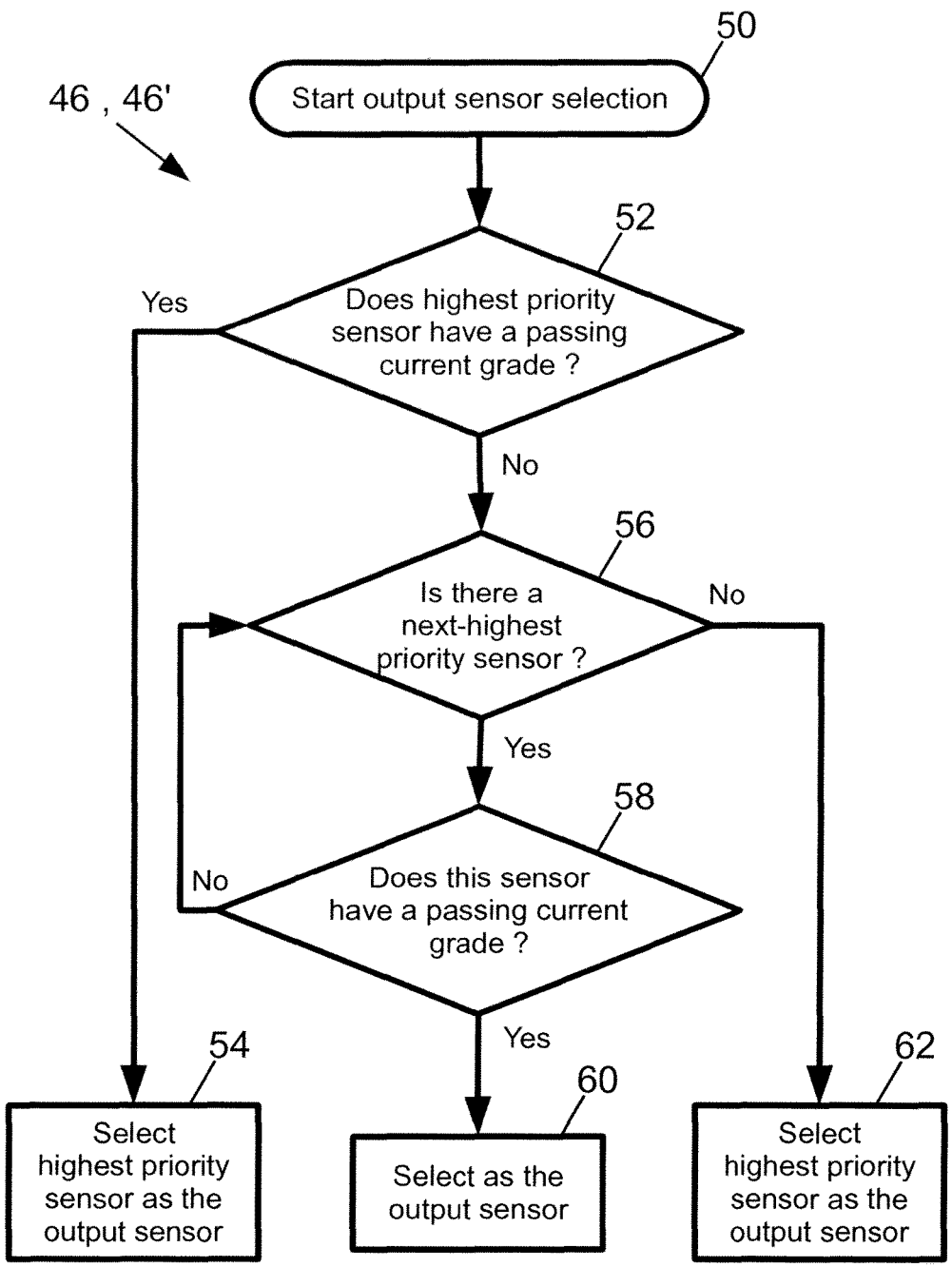

FIG. 2 diagrammatically shows a flow chart for a suitable coordination function for selecting the output sensor from amongst the sensors of FIG. 1.

Figure 3:
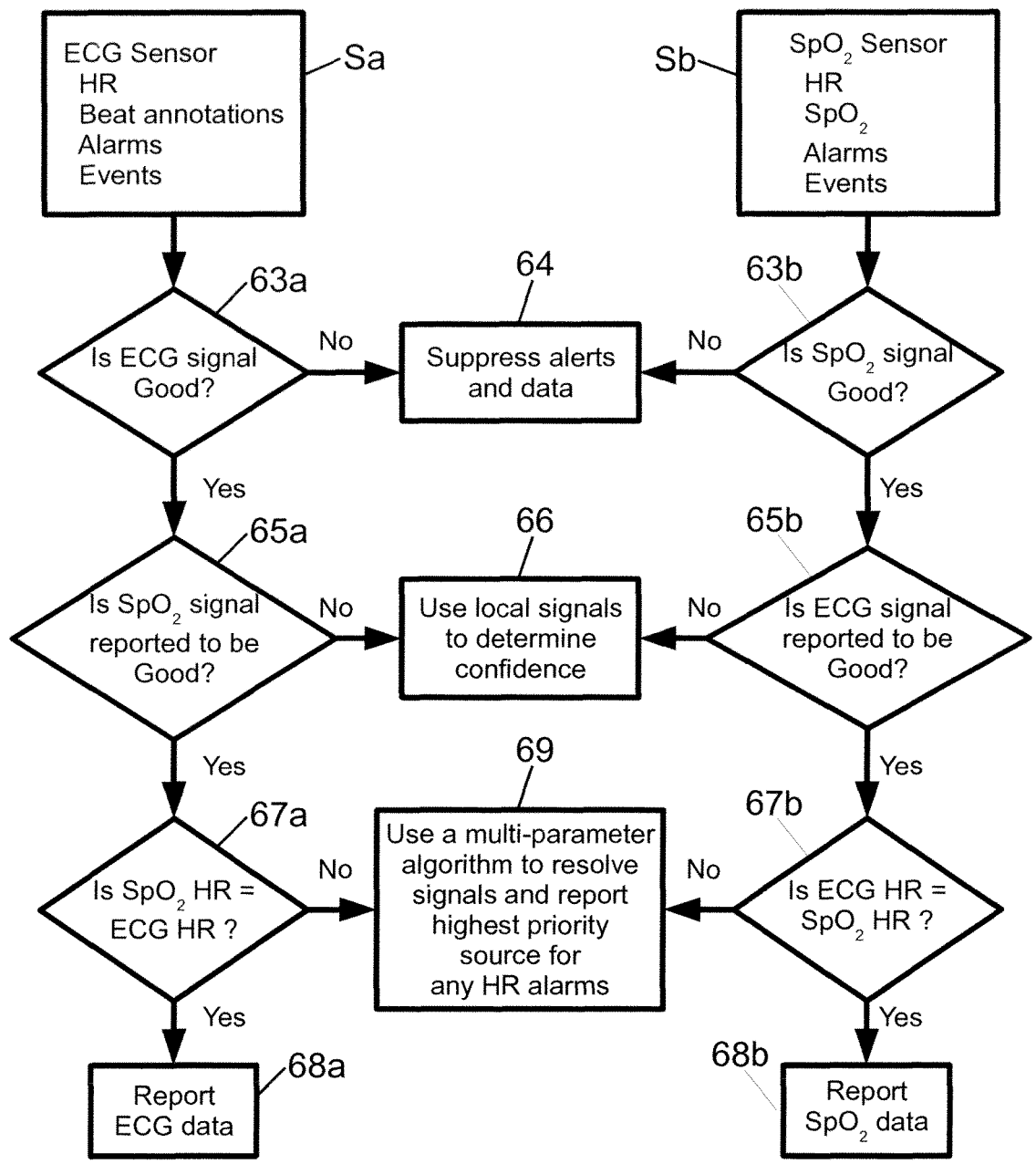

FIG. 3 diagrammatically shows a flow chart for two coordination function instances for selecting the output sensor from amongst the sensors of FIG. 1.

FIGS. 4-6 diagrammatically shows illustrative examples of tabular data structures suitable for storing information pertaining to the sensors of FIG. 1.

Figure 7:
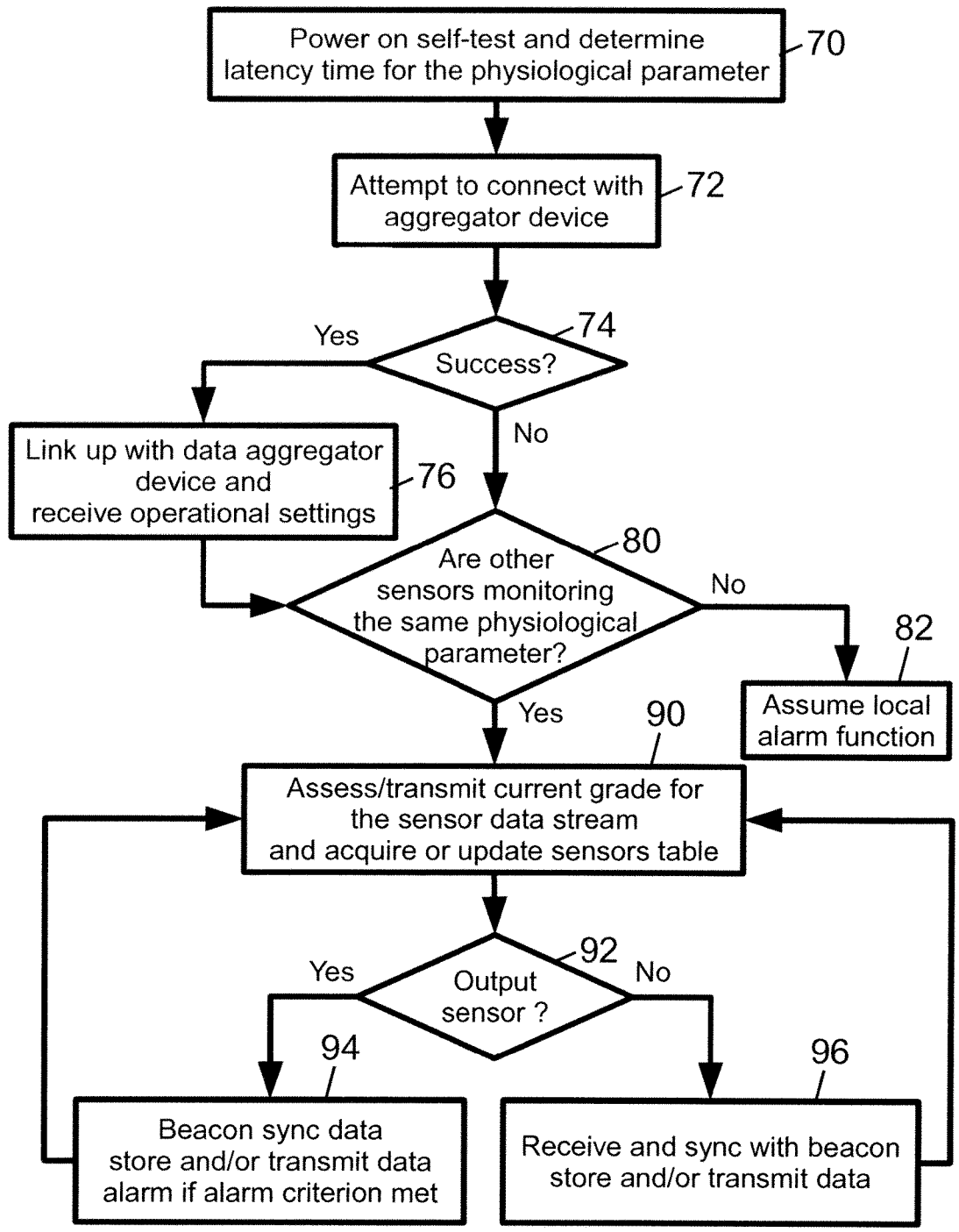

FIG. 7 diagrammatically shows an operational flow chart for a given one of the sensors of FIG. 1.

With reference to FIG. 1, a patient P lying in a bed B is monitored by a plurality of sensors. The bedded location of the patient is merely illustrative, and the techniques disclosed herein are also suitable for ambulatory patients or otherwise-disposed patients. The illustrative sensors include three sensors 2, 4, 6 mounted on the patient's chest and one wrist-mounted sensor 8; however, the sensors can be variously embodied. The illustrative set of sensors 2, 4, 6, 8 is collectively designated herein as a set of sensors 10. For example, an electrocardiographic (ECG) sensor may take the form of a post-mounted ECG monitor connected with the patient via a plurality of electrode leads. As another example, one or more of the sensors may be located partially or wholly internally (that is, inside the patient P)—examples of partially or wholly internally located sensors include a blood pressure (BP) monitor employing an invasive or non-invasive technology, or an internal sensor pacemaker. Some examples of externally mounted sensors include dedicated accelerometer-based heart rate monitors; photoplethysmographic sensors; and ECG monitors employing skin-mounted electrodes.

Each sensor monitors one or more physiological parameters. Some illustrative examples of physiological parameters include: heart rate; respiration rate; electrocardiographic signal; blood oxygenation (or $SpO_2$ level); core body temperature; surface body temperature; or so forth. Some physiological parameters include pulsatile or periodic features—for example, heart rate and respiration rate typically include strong pulsatile features, while an electrocardiographic signal has a strong periodic component. Some physiological parameters do not include pulsatile or periodic features—some illustrative examples include core or surface body temperature.

A given sensor performs a monitoring function that acquires sensor data indicative of at least one physiological parameter. In some cases, the sensor data may be indicative of two or more physiological parameters. For example, a photoplethysmographic sensor acquires sensor data that is indicative of both $SpO_2$ level and heart rate. As another example, an ECG sensor acquires an electrocardiographic signal, which however is also indicative of heart rate (represented by pulsatile and/or periodic components of the electrocardiographic signal. On the other hand, a given sensor may acquire sensor data that is indicative of only a single physiological parameter—for example, a glucose monitor may output a single numerical value (or voltage level, or some other representation) indicative of the current glucose concentration.

The sensor data streams acquired by the various sensors 2, 4, 6, 8 may be utilized in various ways. For example, the set of sensors 10 may communicate their data streams to an optional data aggregator device 12 for display as trend lines, numerical values, or so forth, and/or may be stored as part of the patient's electronic medical record, and/or may be communicated to a monitor 14 at a nurses' station for visual monitoring by medical personnel, and/or so forth. In the illustrative embodiment, the aggregator device 12 is in wireless communication with the nurses' station monitor 14 via a hospital network 16 and wireless access points (AP) 18, 20. Alternatively, a wired or hybrid wired/wireless network can be employed. Communication between the aggregator device 12 and the sensors 10 is also suitably by wired, wireless, or hybrid wired/wireless communication. In some embodiments the communication between the aggregator device 12 and the sensors 10 is by a Zigbee™ or Bluetooth™ compatible wireless protocol.

In the illustrative embodiment, the aggregator device 12 is a multifunction medical monitor 12, for example a bedside or patient room monitor. More generally, the aggregator device 12 can be any device that receives and stores and/or re-transmits the sensor data streams. In particular, the aggregator device 12 does not necessarily provide any visual display of or other output representing the sensor data streams. Moreover, in some embodiments the data aggregator is omitted entirely.

In some embodiments the set of sensors 10 may collectively define a medical body area network (MBAN) of intercommunicating devices, with the aggregator device serving as the hub device for the MBAN. In such MBAN embodiments, the hub/aggregator device may or may not be itself one of the plurality of sensors 10. In wireless MBAN embodiments, the communication between the sensors 2, 4, 6, 8 of the MBAN and the optional aggregator device 12 is by a Zigbee™ or Bluetooth™ compatible wireless protocol, although one or more wired connections are also contemplated. MBAN are also sometimes referred to in the relevant literature by other equivalent terms, such as a capacitively coupled body network, a body area network (BAN), a body sensor network (BSN), a personal area network (PAN), a mobile ad hoc network (MANET), or so forth the term medical body area network (MBAN) is to be understood as encompassing these various alternative terms.

On the other hand, it is also contemplated to omit the aggregator device 12 entirely. In such embodiments, the sensor data streams generated by the sensors 2, 4, 6, 8 may be displayed locally at the sensor—for example, a fingertip $SpO_2$ monitor may include a built-in LCD display showing heart rate and $SpO_2$ level). In some cases, the sensor data stream may not display at all, and the only output is an alarm output (e.g., an audible alarm and/or a flashing light or other visual alarm) generated if the sensor data stream indicates an abnormal value for the monitored physiological parameter. In embodiments in which the aggregator device 12 is omitted, the sensors 2, 4, 6, 8 preferably intercommunicate with each other via wired, wireless, or hybrid wired/wireless communication. For example, the sensors 2, 4, 6, 8 in such embodiments may define an ad hoc MBAN having no hub device, and may again in some suitable embodiments employ a body network such as capicitively coupled data networks, Zigbee™ or Bluetooth™ compatible wireless protocol, optionally further including one or more wired connections.

In some embodiments two or more of the sensors 2, 4, 6, 8 operate independently to acquire different sensor data streams that are indicative of a common physiological parameter. For example, consider the illustrative example in which the sensors 2, 4, 6, 8 include an ECG monitor, a dedicated heart rate monitor, and a plethysmographic sensor (for example, a pulse oximeter mountable on a fingertip or earlobe). Each of these three different sensors acquires a sensor data stream that is indicative of a common physiological parameter, namely heart rate. (The word "common" in "common physiological parameter" is used herein to indicate that the physiological parameter is monitored by more than one sensor, through a variety of technologies; that is, the physiological parameter is "common" to the plurality of sensors 10. The common physiological parameter represents the same physiological value or variation, and is acquired from the same subject, e.g. same patient).

Conventionally, each of these three sensors operate independently, and independently operate to output an alarm if an abnormal heart rate is detected (e.g., a heart rate that is too low, or exhibits an undesirable rythm or an absence of a rythm, or a heart rate that is too high). In some cases, other parameters are acquired in such a way that there are other estimates of heartrate or redundant monitoring. Such redundancy is advantageous insofar as the redundancy improves the confidence in the parameter especially in the presence of noise, such as motion artifacts, and reduces the likelihood of missing a significant physiologic event such as an abnormal heart rate. Independent operation of the sensors 10 has other advantages as well, such as facilitating addition or removal of any one (or more) of the independent sensors 10 monitoring the patient P.

However, it is recognized herein that this conventional approach employing independently operating sensors 10 also has a disadvantage—it substantially increases the likelihood of a false alarm, since any one of the three sensors may output a false alarm if it erroneously detects an abnormal heart rate. Disclosed herein are approaches for maintaining the substantial benefits of having independently operating sensors while avoiding the heretofore concomitant increase in likelihood of false alarms. These approaches retain the advantageous independent operation of the sensors, while counteracting the likelihood of false alarms by coordinating their alarm functions. Additionally, in the case that a sensor is capable of generating a continuous physiologic wave form as part of the generation of data, a sensor which does not produce such a waveform can utilize the wave data generated by another sensor to determine its own signal quality and parameter estimate.

With reference to FIG. 1, each sensor 2, 4, 6, 8 operates independently of the other sensor or sensors of the plurality of sensors 10 in order to perform a set of functions 30 (diagrammatically shown only for the sensor 2, but also performed independently at each of the other sensors 4, 6, 8). The set of functions 30 are suitably implemented by a digital processor, digital controller, digital microprocessor, digital microcontroller, application-specific integrated circuitry (ASIC), field-programmable gate array (FPGA), or other hardware or combination of hardware, that is configured to perform the functions 30. The hardware is optionally configured to perform the functions by suitable software or firmware residing on a suitable read-only memory (ROM), random access memory (RAM), programmable read-only memory (PROM), or other electronic memory, or on a magnetic or optical memory. In diagrammatic FIG. 1, the set of functions 30 is diagrammatically indicated for only one sensor 2 of the plurality of sensors 10, but it is to be understood that each sensor 2, 4, 6, 8 independently performs the set of functions 30.

In general, each sensor should implement the following functionality: acquire data (including a waveform and/or alert state) for the common physiological parameter; determine the data time offset from an external time master (relevant for a sensor generating continuous wave data); obtain (or store) knowledge of absolute priority of all sensors respective to the common physiological parameter; determine a current state of acquired data (without reference to data from other sensors); obtain knowledge of the current state of other sensor data for patient P respective to the common physiological parameter; and internally update the acquired data state given the data and states of the other sensors.

This functionality is performed by the illustrative set of functions 30 as follows. A monitoring function 32 is implemented by which the sensor acquires sensor data indicative of the common physiological parameter. The acquired sensor data may include continuous waveform, or discrete data (e.g., pulse occurrences), and may optionally include acquisition or determination of an alert state. The monitoring function 32 typically utilizes a sensor element (not shown) of the sensor in order to generate the sensor data indicative of the common physiological parameter. For example, in an ECG monitor the monitoring function of the sensor employs a set of electrodes to acquire ECG data that is indicative of (at least) heart rate. In a pulse oximeter the monitoring function of the sensor measures a transmittance ratio for light of two different wavelengths (e.g., red and infrared) to acquire pulse oximeter data that is indicative of (at least) heart rate. These are merely illustrative examples.

In the illustrative embodiment, the set of functions 30 also includes a reporting function 34 by which the sensor conveys sensor data acquired by the monitoring function of the sensor to the data aggregator device 12. In the illustrative example the data aggregator device 12 is a bedside monitor; however, as noted previously the data aggregator can be otherwise-embodied, for example as the hub device of an MBAN including the plurality of sensors 10. In embodiments in which the data aggregator device 12 is omitted, the reporting function 34 is inoperative or may optionally be omitted, or alternatively may convey sensor data directly to other sensors of the set of sensors 10.

The illustrative set of functions 30 further includes at least one output function 36, which is different from the reporting function 34. In some embodiments the at least one output function 36 includes an alarm function that outputs an alarm responsive to an alarm condition. The alarm condition includes sensor data acquired by the monitoring function 32 of the sensor indicating an abnormal value for the common physiological parameter—but the alarm condition additionally includes a further condition that represents that no other sensor monitoring the common physiological parameter is showing a normal reading for the common physiological parameter. In other embodiments the at least one output function 36 additionally or alternatively includes some other output function that again is performed only conditionally.

The illustrative set of functions 30 further include a grading function 38 and a synchronization function 40. The grading function 38 of a given sensor determines the current state of acquired data (without reference to data from other sensors). The synchronization function 40 determines the data time offset from an external time master, and again is relevant for a sensor generating continuous wave data.

With continuing reference to FIG. 1, the likelihood of false alarms is reduced by coordinating the alarm functionality amongst the plurality of independently operating sensors 10 that monitor the common physiological parameter. Toward this end, a data structure 44 is maintained at the aggregator device 12 (or, alternatively, if the aggregator device is omitted then a data structure instance 44' is maintained at each sensor 2, 4, 6, 8). The data structure 44, 44' stores sensor information including at least (1) priorities of the plurality of sensors 10 respective to the common physiological parameter and (2) current grades for the sensors of the plurality of sensors 10. In the illustrative example the common physiological parameter is heart rate. However, the common physiological parameter may be another parameter such as respiration, breathing rate, or core body temperature as three other illustrative examples. Based on the content of the data structure 44, 44' including the priorities of the sensors and their current signal quality as indicated by the current grades, a coordination function 46 executing at the aggregator device 12 determines the "best" current sensor for monitoring the common physiological parameter. Alternatively, if the aggregator device is omitted then a coordination function instance 46' executes at each sensor 2, 4, 6, 8 to determine the "best" current sensor for monitoring the common physiological parameter.

The coordination of the sensors respective to the common physiological parameter is based on the time invariant priorities of the sensors augmented by the current (and in general varying with time) signal quality metrics (i.e., grades) of the sensors. Considering the priority first, this is a time-invariant metric or absolute or relative ranking indicating the robustness of each sensor 10 for monitoring the common physiological parameter. The priority does not, however, take into account the current operational states of the sensors. For example, the dedicated heart rate monitor may have the highest priority insofar as it is considered the "best" sensor for monitoring heart rate—but, at any given time the dedicated heart rate monitor may be malfunctioning, improperly connected with the subject, or otherwise producing unreliable data or data of reduced reliability. By way of illustrative example, Table 1 provides priority rankings for various signal sources for the heart rate (HR) and respiration common physiological parameters. In this illustrative example, it is seen that for the HR parameter the internal ECG electrode has the highest priority (1), the pacemaker has the next highest priority (2), the surface ECG electrode has the next highest priority (3), and so forth. These priorities reflect the expected robustness of the devices for monitoring heart rate, but do not reflect the current operational state. It will be noted that internal sensors (e.g., the internal ECG electrode and the pacemaker) have highest priority, reflecting the fact that such internal sensors tend to be less prone to interference and more likely to yield accurat heart rate information.

TABLE 1

Priorities from similar physiologic measures

| Parameter | Derived from | Signal source | Priority |
|---|---|---|---|
| HR | ECG wave | Surface Electrode | 3 |
| HR | ECG wave | Internal Electrode | 1 |
| HR | Oscillatory wave | Distal finger cuff | 6 |
| HR | NIBP pulse | NIBP cuff | 7 |
| HR | Accelerometer | Chest | 5 |
| HR | Beat rate | Pacemaker | 2 |
| HR | PPG Pulse | SpO2 PPG | 4 |
| Respiration | Resp Wave | ECG Impedance | 7 |
| Respiration | Resp Wave | Abd/Thorax Belt | 6 |
| Respiration | Resp Wave | QRS peak area | 9 |
| Respiration | EMG Resp | Surface Electrode | 5 |
| Respiration | EMG Resp | Internal Electrode | 4 |
| Respiration | PPG Resp | SpO2 PPG | 11 |
| Respiration | Accelerometer | Chest/Abdomen | 10 |
| Respiration | Acoustic | Neck/Chest | 8 |
| Respiration | Air Flow | Mouth/Nose/Stoma | 2 |
| Respiration | CO2 Wave | Mouth/Nose/Stoma | 1 |
| Respiration | External device | Ventilator/CPAP | 3 |

These priorities reflect the expected accuracy of the device, but they do not reflect the current operational state, which might bias toward relying upon a lower priority device if its current signal quality is higher than that of a higher priority device.

To incorporate the (in general) time-varying signal quality into the coordination of the sensors, a current signal quality grade is assigned for each sensor, which is indicative of current signal quality of the monitoring function of the sensor. The current signal quality grade for the monitoring function 32 of each sensor is generated by the grading function 38 of that sensor. Various grading algorithms can be employed. For example, if the sensor data is expected to have a certain periodicity, then a fast Fourier transform (FFT) or other spectral analysis can be employed to detect dominant periodicity or periodicities and compare these with an expected range of reasonable periodicities for the sensor data. In the case of a constant value, such as a temperature reading, the grading function 38 may employ simple thresholds—if the sensor data are above a maximum threshold or below a minimum threshold, then the grading function 38 indicates a malfunctioning operational status. In some embodiments the grading function 38 outputs a binary "pass" or "fail" grade, while in other embodiments the grading function 38 outputs a multilevel grade or even a continuous grade (e.g., a grade in a continuous range [0,1]). In some embodiments, the grading function 38 cannot distinguish between a "malfunction" of the sensor and an abnormal value for the common physiological parameter. Indeed, it is not necessary that the grading function 38 be able to make this distinction.

The information contained in the data structure 44 or data structure instance 44', including at least the priority and the current grade for each sensor, is used by a coordination function 46 or coordination function instance 46' to select one output sensor from amongst the plurality of sensors 10.

As already noted, the coordination function 46, 46' may be variously embodied. In some embodiments, the coordination function 46 is performed by the aggregator device 12. In these embodiments the coordination function 46 is suitably implemented by a digital processor, digital controller, digital microprocessor, digital microcontroller, ASIC, FPGA, or other hardware or combination of hardware, of the aggregator device 12. The hardware is optionally configured to perform the functions by suitable software or firmware residing on a suitable ROM, RAM, PROM, or other electronic memory, or on a magnetic or optical memory. In other embodiments an instance of the coordination function 46' is performed by each sensor of the plurality of sensors 10. In these embodiments each coordination function instance 46' is suitably implemented by a digital processor, digital controller, digital microprocessor, digital microcontroller, ASIC, FPGA, or other hardware or combination of hardware, of the sensor. The hardware of the sensor is optionally so configured by suitable software or firmware residing on a suitable ROM, RAM, PROM, or other electronic memory, or on a magnetic or optical memory. Each coordination function instance 46' is identical, and accordingly it is expected that in such embodiments all sensors of the plurality of sensors 10 will select the same output sensor. The use of multiple coordination function instances 46' at the various sensors is employed to enable ad hoc addition or removal of sensors (for example, in an MBAN) while maintaining the coordination function 46' at all operating sensors of the MBAN. In some embodiments, operation may switch between (1) performing the coordination function 46 at the aggregation device 12 when such a device is available and (2) performing multiple coordination function instances 46' at the sensors when no aggregation device is available.

With reference to FIG. 2, an illustrative embodiment of the coordination function 46 (or coordination function instance 46') is diagrammatically shown. Execution of the coordination function 46, 46' is initiated at a start operation 50. In a first decision block 52, it is determined whether the highest priority sensor (as indicated by the priorities stored in the data structure 44 in embodiments employing the aggregator device 12, or in the individual data structure instances 44' stored at all sensors 2, 4, 6, 8 in embodiments in which the aggregator is unavailable) has a passing current grade (based on the current grades also stored in the data structure 44 or data structure instances 44'). Said another way, first decision block 52 determines whether the "best" sensor for monitoring the common physiological parameter is currently operating correctly. If so, then in a selection operation 54 the highest priority sensor is selected as the output sensor.

If the first decision block 52 determines that the highest priority sensor does not have a passing grade, then at a second decision block 56 it is determined whether there is a next highest priority sensor. If there is a next highest priority sensor, then the process flow moves to a third decision block 58 at which it is determined whether this (next-highest priority) sensor has a passing current grade. If it does have a passing grade, then in a selection operation 60 that (next highest priority) sensor is selected as the output sensor. Said another way, the blocks 56, 58, 60 determine that, although the highest priority sensor is not currently functioning properly, there is a next-highest priority sensor that is functioning properly and that sensor should be selected as the output sensor.

On the other hand, if the third decision block 58 determines that the next-highest priority sensor is also not functioning properly (that is, has a failing current grade), then flow passes back to the second decision block 56 to consider the sensor next down on the prioritization list, and so forth, until a sensor is found by the third decision block 58 that has a passing grade which is therefore assigned as the output sensor by the selection block 60.

Typically, the described operation of the decision blocks 52, 56, 58 will lead to selection of a single output sensor, corresponding to the highest-priority sensor that has a passing current grade. However, there remains the possibility that no sensor of the plurality of sensors 10 has a passing grade. In such a case, the decision blocks 52, 56, 58 will iterate until the second decision block 56 indicates that there are no more sensors to consider. At this point, there are two possibilities: (1) all the sensors are malfunctioning, or (2) the common physiological parameter indeed has an abnormal reading which is causing all the sensors to have failing current grades. (The latter possibility arises only if the grading functions 38 of all the sensors are incapable of distinguishing between a sensor failure and an abnormal reading for the common physiological parameter.) Of these, possibility (2) is usually the more likely possibility, since possibility (1) requires the coincidence of multiple simultaneous sensor failures. On the other hand, it is possible that one or more of the sensors has indeed failed. In any event, this is a unusual situation that should be reviewed by human medical personnel.

Accordingly, in the illustrative embodiment if the second decision block 56 indicates that there are no more sensors to consider then at a selection operation 62 the highest priority sensor is selected as the output sensor. The effect of this is that a single sensor will alarm. It will be appreciated that the selection operation 62 can be replaced by or augmented with another suitable operation. For example, in embodiments in which the coordination function 46 is embodied by an aggregator device, another alternative is to have the aggregator device perform an alarm operation.

The coordination function 46 (or each coordination function instance 46') is suitably executed occasionally, for example every ten seconds, or every five seconds, or every minute, or every five minutes, or on some other time basis, or executes whenever a sensor grade changes. Similarly, the grading function 38 is suitably invoked to update the current grade for the sensor on an occasional basis, e.g. every few seconds, or every minute, or every few minutes, or so forth, or responsive to an indication that the signal quality has changed. Between executions of the coordination function 46 (or instance 46'), the selected output sensor continues to operate as the output sensor. In embodiments in which the grading function 38 cannot distinguish between a malfunctioning sensor and an abnormal reading for the common physiological parameter, it is known that at the time the coordination function 46 selected the output sensor that sensor was acquiring a normal reading for the common physiological parameter.

With reference to FIG. 3, a further illustrative example is shown, in which two sensors, namely an ECG sensor Sa and an SpO$_2$ sensor Sb, operate to produce heart rate data of enhanced reliability. In an operation 63a, 63b executing on sensors Sa, Sb respectively, it is determined whether the sensor currently has good signal quality (i.e., currently has a passing current signal quality grade). If not, then an operation 64 is performed which suppresses alerts from that sensor. Assuming the sensor does have good signal quality, then in an operation 65a, 65b executing on sensors Sa, Sb respectively, it is determined whether the other sensor (e.g., the SpO$_2$ sensor Sb in the case of operation 65a executing on the ECG sensor Sa) is also reported to have good signal quality (i.e., is also reported to have a passing current signal quality grade). If not, then an operation 66 is performed which uses only local signals to determine confidence, i.e. to update the current signal quality grade. On the other hand, if the other sensor also has a passing grade, then in an operation 67a, 67b executing on sensors Sa, Sb respectively, it is determined whether the other sensor is reporting the same value for the common physiological parameter (heart rate in the instant example). If yes, then in an operation 68a, 68b executing on sensors Sa, Sb respectively, the respective ECG data and SpO$_2$ data are reported. If the operations 67a, 67b produce a negative result, that is, the two sensors are generating different heart rate values, then in an operation 69 a multi-parameter algorithm is used to resolve the difference in the signals and report the highest priority source for any heart rate alarms. The multi-parameter algorithm is based on the time invariant priority levels of the two sensors Sa, Sb augmented by the current signal quality grades of the two sensors Sa, Sb.

If the selected output sensor suddenly acquires an abnormal reading, then it would, in the absence of coordination with other sensors, begin alarming. However, if the abnormal reading is due to a malfunction of the selected output sensor (where "malfunction" includes both internal malfunctions of the sensor itself and "malfunctions" caused by disconnection of an electrode or other loss of operative connection with the subject), then the alarming should be suppressed. Toward this end, the abnormal reading triggers execution of the coordination function 46 (or, in other embodiments, the coordination function executes iteratively on a sufficiently rapid basis to be essentially "real-time"). Execution of the coordination function 46 detects the abnormally functioning sensor (based on the observation that other sensors monitoring the same physiological parameter are not reporting an abnormal reading) and selects a new output sensor that is generating a normal reading for the common physiological parameter. Hence the false alarm is prevented.

On the other hand, if the abnormal reading is "real", that is, due to the common physiological parameter actually taking on an abnormal reading, this will affect all the sensors. Thus, the highest priority sensor is selected as the output sensor (as per selection operation 62, see FIG. 2) and will begin (correctly) alarming. This is not a false alarm—this is a correct alarm alerting medical personnel of an abnormal reading of the common physiological parameter.

With this approach, the only way a false alarm can occur is if every sensor of the plurality of sensors 10 monitoring the common physiological parameter fail simultaneously. This is an unlikely event.

With returning reference to FIG. 1 and with further reference to FIGS. 4-6, an illustrative "tabular" embodiment of the data structure 44 (or data structure instance 44') is shown. In this embodiment, the data structure is a table having the following columns: "Sensor"; "Latency time"; "Priority"; "Current grade"; and "Output?". The "Latency time" stores the delay between the physiological parameter and its time stamp in the data stream generated by the sensor. It can be hard-coded based on precision manufacturing of the sensor, or may be determined at start-up when the sensor powers on. The "Priority" column stores the time invariant priority rating for each sensor: in the illustrative example, the dedicated heart rate sensor ("HR") has the highest priority (priority=1), the ECG sensor has the next-highest priority (priority=3), and the oximeter sensor has the lowest priority (priority=7). These priorities are time invariant and do not change based on the operational status of the sensors.

The "Current grade" is the current grade assigned by the grading function 38 of each sensor. In the embodiment of FIGS. 4-6 the grade is a binary value (i.e., "pass" or "fail"; more generally, however, the grade may be a continuous variable, and/or may have different thresholds or scales based on the application area, patient history, or other pertinent information). The "Output ?" column indicates whether the sensor is selected as the output sensor.

FIG. 4-6 provide an example-based illustration of operation of the coordination function 46 (or coordination function instance 46') described in FIG. 2. In FIG. 4, the current grade for all three sensors is "Pass", and so as per selection block 54 the highest-priority "HR" sensor is selected as the output sensor for the heart rate. In FIG. 5, the "HR" sensor has a failing current grade whereas the remaining two lower-priority sensors have passing current grades. Thus, as per selection block 60 the ECG sensor which is the highest priority sensor having a passing grade is selected as the output sensor for the heart rate. Finally, in FIG. 6 all three sensors have failing current grades. Thus, as per selection block 62 the highest priority sensor (the "HR" sensor in the example of FIGS. 4-6) is selected as the output sensor, and will alarm.

In the foregoing, it is assumed that all sensors are operational at least to the extent that they can execute their respective grading functions 38 and communicate the current grades to the other sensors. If a sensor fails to report entirely, then the current grade for that sensor is assumed to be a failing grade. Also, the illustrative embodiment of the coordination function 46, 46' described with reference to FIGS. 2-6 assumes binary grading, i.e. each sensor having a current grade of either "pass" or "fail". If a grading scheme with finer gradations is employed (e.g., a continuous grade scale of [0,1] where 1 is the highest grade and means the sensor is generating a highly reliable data stream whereas 0 is the lowest grade and indicates the sensor is not communicating at all), then the coordination function 46 can be modified to utilize this additional information. For example, in one approach for utilizing the aforementioned [0,1] grading scale, the decision blocks 52, 58 are suitably modified to make their decisions by comparing a product or other combination of the sensor priority and the current signal quality grade with a decision threshold. Such an approach implements a "sliding scale" in which the highest priority sensor could be selected as the output device even if it has a relatively low current grade, whereas a sensor with a lower priority could only be selected as the output device if its current grade is high while the higher priority sensors have substantially lower grades.

The foregoing has considered operation respective to the "alarm" output operation. The disclosed coordination between sensors can also be advantageously used for other purposes. In some embodiments, the at least one output function 36 additionally or alternatively includes a beaconing function. Some types of common physiological parameter are expected to have a pulsatile or periodic feature that is expected to repeat occasionally. The repetitions are typically regular, although such regularity is not necessary for these embodiments. Some examples of a pulsatile or periodic feature include: a pulse corresponding to a cardiac ventricle contraction; a feature corresponding to inhalation in a respiratory parameter; a generally sinusoidal variation; or so forth. Even a physiological parameter that does not have a pulsatile or periodic component will typically have temporal variation and time-varying features, for example due to patient motion or so forth.

The purpose of the beaconing function is to provide a beacon signal at a synchronization time for synchronizing the various sensor data streams that are indicative of the common physiological parameter. One reason such synchronization is valuable is that different sensor data streams may have different latency times between the acquisition of the common continuous physiological parameter and the availability of the indicative sensor data stream to the coordination function 46. In the illustrations of FIGS. 4-6, for example, the dedicated heart rate ("HR") sensor has a 0 msec latency (that is, no significant latency), the ECG monitor has a 35 msec latency, and the oximeter has a 7.0 msec latency. Such latencies can result from signal transmission delays (e.g., capacitive or inductive delays), data processing delays, or so forth, delays introduced by communication protocols, or so forth.

With returning reference to FIG. 1, in embodiments employing beaconing, the at least one output function 36 includes a beaconing function that is performed only if the sensor is selected as the output sensor (that is, the highest priority sensor having a passing current signal quality grade, or in some embodiments the sensor having the highest combination of priority and current signal quality grade). If the sensor is selected as the output sensor, then the beaconing function outputs a beacon signal at a synchronization time to the other sensor or sensors of the plurality of sensors 10 indicating a time of occurrence of a pulsatile or periodic feature of the common physiological parameter (or, more generally, a synchronization time). The sensor or sensors that are not selected as the output sensor perform the sync function 40, which shifts a time base of sensor data acquired by the monitoring function of the sensor based on the received beacon signal and the latency times of the sensor and the selected output sensor. Considering the situation of FIG. 5 as an illustrative example, here the output sensor is selected as the ECG sensor, which has a 35 msec latency time. The only other currently operating sensor is the oximeter sensor, which has a 7.0 msec latency time. Thus, when the oximeter sensor receives a beacon signal it performs a time base shift of +28 msec to match up with the time axis of the ECG sensor which is the selected output sensor. Optionally, the sync function 40 may additionally perform a linear smoothing transition (or other smoothing transition) in the time base shift between successive beacon signals if they indicate slightly different time base shifts. (It is generally expected that successive beacon signals will indicate similar or even identical time base shifts).

With reference to FIG. 7, an illustrative process flow for a single sensor is diagrammatically shown. In a startup operation 70, the sensor is turned on, optionally performs a power-on self-test, and optionally performs other calibrations such as an optional latency time calibration. In an operation 72, the sensor attempts to connect with an aggregator device. A decision block 74 determines whether this attempt was successful. If so, then in an operation 76 the sensor links up with the aggregator device and receives operational parameters from the aggregator device.

In a decision block 80, the sensor determines whether other sensors are monitoring the same (i.e., common) physiological parameter. If the sensor is linked up with an aggregator device, the decision block 80 can suitably query the aggregator device to make this determination. On the other hand, if there is no aggregator device then the sensor can employ a wireless protocol (e.g., Zigbee™ or Bluetooth™) to poll for other sensors assigned to the patient P, and if such another sensor is found to share information with the other sensor in order to establish whether the other sensor is monitoring the same physiological parameter of the same patient (i.e., is monitoring a common physiological parameter). If the decision block 80 is unable to identify any other sensors monitoring the common physiological parameter, then in an operation block 82 the sensor assumes local alarm function and operates independently as an isolated sensor (albeit possibly linked up with an aggregator device).

On the other hand, if one or more other sensor devices are identified which are monitoring the common physiological parameter, then an embodiment of the disclosed approaches for coordinating the sensors is implemented. Toward this end, an operation 90 includes invoking the grading function 38 to determine a current signal quality grade for the sensor data stream indicative of the common physiological parameter and transmitting the current signal quality grade to the aggregator device and/or to the other sensor or sensors. If a coordination function instance 46' is run locally at each sensor, then the operation 90 suitably further includes receiving the current signal quality grade or grades from the other sensor or sensors and creating or updating the sensors table instance 44' stored at the sensor. At a decision block 92, the sensor determines if it is selected as an output sensor. In embodiments in which the coordination function 46 is executed at the aggregator device 12, the decision block 92 entails receiving the selection of the output sensor from the aggregator device 12. On the other hand, in embodiments in which a coordination function instance 46' is run locally at each sensor, that local function instance 46' determines whether the sensor is selected as the output sensor.

If the sensor is selected as the output sensor as indicated by the decision block 92, then in an operation 94 the sensor executes the beaconing function to output the beaconing signal. Optionally, the operation 94 also includes execution of the optional reporting function 34 to convey the sensor data stream to the aggregator device 12. On the other hand, if the sensor is not selected as the output sensor then in an operation 96 the sensor receives the beaconing signal and executes the sync function 40, and optionally executes the optional reporting function 34 to convey the sensor data stream to the aggregator device 12. Flow then returns to block 90 to iterate. It is noted that the optional reporting function 34 is performed regardless of whether the sensor is selected as an output sensor.

While the process of FIG. 7 is described for sensor startup, it will be appreciated that the process may be repeated if there is a state change in the set of functions 30, so that if the grading of the highest priority changes, the system will determine the best course of action. To ensure detection of any aggregator, such a repetition suitably loops back to the aggregator search operation 72.

In the illustrative examples, each sensor of the plurality of sensors 10 operates independently to generate an independent sensor data stream indicative of the common physiological parameter. In this case, there is a one-to-one correspondence between (i) the independent sensor data streams indicative of the common physiological parameter and (ii) the independently operating sensors. However, more generally two or more of the various independent sensor data streams indicative of the common physiological parameter may be generated by the same sensor device. The disclosed approaches remain apropos, with slight notational changes (e.g., the coordination function 46, 46' selects an output sensor data stream rather than an output sensor, and each set of functions 30 is associated with an independent sensor data stream rather than with an independently operating sensor, and so forth).

With returning reference to FIG. 1, the common physiological parameter is monitored by the monitoring function 32 of each sensor. The monitoring function 32 generates a continuous high fidelity waveform emanating from the same patient (such as ECG, Plethysmogram, respiration, other pulsatile waveforms). The waveform may have pulsatile or periodic features following pulsatile or periodic features of the indicated common physiological parameter.

Coordination employs absolute or relative priority values for the plurality of sensors monitoring the common physiological parameter. The priority values are based on the expected fidelity of the sensors. For example, an ECG sensor is generally expected to be more reliable than pleth for heart rate, and thus the ECG sensor has a higher priority than the pleth. Similarly, an airflow sensor is expected to be more reliable than an accelerometry sensor for respiration, and so forth. These priority values are time invariant and do not account for operational status. To account for the current operational status of each sensor, a suitable "per sensor data stream" confidence algorithm (i.e., grading function) is employed to assess current sensor operational status and to assign a current signal quality grade for each sensor.

The coordinating of the sensors also optionally entails time synchronization. In some embodiments, a deterministic parameter acquisition overhead is assumed, that is, a fixed latency delay is assumed for the acquisition and signal processing. This enables beaconing as disclosed herein to synchronize the time bases of the various sensor data streams. Parameter beaconing is performed between measurements, or from the aggregator device. The beaconing outputs a beacon signal to the sensors (other than the output sensor). The beacon signal serves as a time sync signal and is derived from highest level real-time waveform available from the patient. Relative offset corrections are made for each sensor data stream from last sync beacon for significant observations such as peak amplitude signal, or low confidence signal.

From the perspective of a given sensor, the disclosed approaches enable the sensor to "understand" what measurements are available for the patient, if there is a central alarm management system or is everything announced locally at the patient, and if other sensors are working for the same patient and for the same common physiological parameter. Under the assumption that the given sensor is one of several sensors used for the patient and it is required to perform local alarms (i.e. there is no exclusive central or remote alarm system), the sensor self resolves which sensor should be the output sensor for beaconing and depending on what other sensors are available for the patient P the sensors are able to each locally perform the coordination function 46' to determine whether it should be the source of the beacon signal for synchronization of the plural sensors, or if it should follow another sync source. Optionally, the synchronization includes using similar parameters from multiple sensors monitoring the common physiological parameter to derive a single high confidence alarm source for the common physiological parameter. (See, e.g., FIG. 3).

If the given sensor is the sync source, it beacons a periodic sync signal (or, more generally, a beacon signal that may or may not be periodic but which is indicative of an occurrence of a pulsatile or periodic feature of the common physiological parameter, for example the R-wave of an ECG signal or so forth) and the sensor references its sensor data stream as an offset from the last sync signal. The given sensor also suitably listens for other signals it can use to improve the alarm calls it makes (such as listen for, and sync the pleth wave as part of deciding ECG alarms). The given sensor also suitably listens for other sensors coming and going for the patient (i.e. another sensor will take over the beaconing, or leaves the patient's service).

If the given sensor is part of a central or remote alarm system, it would not necessarily need to process other signals locally, but instead can send its data to the aggregator device referencing the current time sync offset for its data (be it this sensor or another sensor as the beaconing source).

In an illustrative example, the following heuristics are involved: (1) POST and start up; (2) start acquiring physiologic signals and optionally measure data acquisition latency; (3) attempt association with an aggregator device and other sensors; (4) if no other sensors are identified, assume local alarming per capabilities; (5) if connection is made with an aggregator device, then receive list of other parameters already acquired for this patient based on a patient identification or from the aggregator device if available; (6) if multiple sensors are monitoring the common physiological parameter then determine which sensor is highest reliability measurements; (7) if the given sensor has the highest reliability measurements then start data sync beaconing for other sensors; (8) otherwise, look for data sync beaconing for this patient; (9) report serialized data with offset from specific serialized time sync message; (10) at the aggregator device receive asynchronous wave packets for patient; and (11) reassemble the wave information aligned from the same time sync.

In embodiments employing the beaconing function and the sync function, downstream applications have multiple sensor data streams indicative of the common physiological parameter, which are aligned in time based on the beaconing/sync operations, available for further processing. This enables the downstream applications to select the best data stream, correlate or combine the time-synced data streams, or otherwise utilize the data redundancy.

In some embodiments, the approach is to send only the peak detections with an offset from the last sync for a pulsatile waveform thus reducing the amount of data needing to be broadcast and processed. Said another way, the reporting function 34 may optionally only convey the peak detections. Such an approach may be efficient and useful if the downstream applications utilize only the peak information (e.g., to monitor heart rate).

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. A system comprising:
a plurality of sensors, each sensor of the plurality of sensors operating independently of the other sensor or sensors of the plurality of sensors, each of the sensors including a data structure configured to store information related to the corresponding sensor, a transceiver configured to send and receive data from the other sensors of the plurality of sensors, a processor; and a memory configured to store machine-executable instructions, wherein execution of the instructions causes each sensor to perform at least:
 a monitoring function acquiring sensor data indicative of a common physiological parameter, and
 a grading function performed occasionally at a predetermined time pattern to assign a current grade for the sensor wherein the current grade is indicative of operational status of the monitoring function of the sensor; and
wherein the data structure stores information pertaining to the plurality of sensors including at least priorities of the plurality of sensors respective to the common physiological parameter and the current grades for the sensors of the plurality of sensors, the priorities including (i) robustness versus interferences of the plurality of sensors respective to the common physiological parameter and (ii) the current grades for the sensors of the plurality of sensors;
wherein execution of the instructions further causes each sensor of the plurality of sensors to perform at least one output function generating an output signal conditional upon content of the data structure including at least the priorities and the current grades of the sensors of the plurality of sensors indicating the output function should be performed.

2. The system as set forth in claim 1, wherein execution of the instructions stored in the memory of each of the sensors causes each sensor to perform an alarm function that outputs an alarm responsive to an alarm condition dependent on at least:
 sensor data acquired by the monitoring function of the sensor indicating an abnormal value for the common physiological parameter, and
 content of the data structure including at least the priorities and the current grades of the sensors of the plurality of sensors
wherein the alarm is audibly with an audible alarm or visually output with a flashing light.

3. The system as set forth in claim 1, wherein execution of the instructions stored in the memory each of the sensors causes each sensor to acquire a latency time;
 wherein the data structure further stores the acquired latency time for each sensor, and execution of the instructions stored in the memory of each of the sensors causes the sensor to perform a beacon function performed conditional upon the sensor being the selected output sensor wherein the beacon function outputs a beacon signal to the other sensor or sensors of the plurality of sensors indicating a synchronization time;

wherein execution of the instructions stored in the memory each of the sensors causes each sensor of the plurality of sensors to perform a sync function performed conditional upon the sensor not being the selected output sensor that shifts a time base of sensor data acquired by the monitoring function of the sensor based on the synchronization time and the latency times of the sensor and the selected output sensor.

4. The system as set forth in claim 1, further comprising:
a medical monitor including a data structure configured to store information related to the medical monitor, a transceiver configured to send and receive data from the sensors of the plurality of sensors, a processor; and a memory configured to store machine-executable instructions;
wherein execution of the instructions stored in the memory of the medical monitor further causes the medical monitor to perform a coordination function selecting an output sensor from the plurality of sensors based on content of the data structure including at least the priorities and the current grades of the sensors of the plurality of sensors;
wherein the at least one output function of each sensor of the plurality of sensors is not performed if the sensor is not selected as the output sensor.

5. The system as set forth in claim 4, wherein the execution of the instructions stored in the memory of the medical monitor causes the transceiver of the medical monitor to convey the selection of the output sensor to the transceivers of each sensor of the plurality of sensors.

6. The system as set forth in claim 4, wherein execution of the instructions stored in the memory of the medical monitor further causes the medical monitor to perform a reporting function in which the transceiver of the medical monitor receives sensor data acquired by the monitoring function of the sensor from the corresponding transceivers of the sensors, the reporting function being different from the at least one output function.

7. The system as set forth in claim 1, wherein the execution of the instructions stored in the memory each of the sensors causes the plurality of sensors to perform a coordination function a coordination function selecting an output sensor from the plurality of sensors based on content of the data structure including at least the priorities and the current grades of the sensors of the plurality of sensors by operations including:
controlling the corresponding wireless transceiver to transmit the current grade for the sensor to the other transceivers of the other sensors of the plurality of sensors,
controlling the corresponding wireless transceiver to receive the current grade from the corresponding transceivers for each other sensor of the plurality of sensors,
constructing an instance of the data structure at the sensor, and
selecting an output sensor from the plurality of sensors based on content of the data structure including at least the priorities and the current grades of the sensors of the plurality of sensors.

8. The system as set forth in claim 7, the wireless transceivers of each the sensors of the plurality of sensors are in communication with each other via a hospital network and at least one access point.

9. The system as set forth in claim 7, wherein execution of the instructions stored in the memory of each of the sensors causes each sensor to perform a reporting function in which each sensor conveys sensor data acquired by the monitoring function of the sensor to the other sensors of the plurality of sensors, the reporting function being different from the at least one output function, the reporting function being performed each sensor regardless of whether or not the sensor is the output sensor.

10. An apparatus comprising:
a sensor including a data structure configured to store information related to the sensor, a transceiver configured to send and receive data from other devices, a processor; and a memory configured to store machine-executable instructions, wherein execution of the instructions causes the sensor to perform:
a monitoring function acquiring sensor data indicative of a common physiological parameter,
a grading function assigning a current grade for the sensor that is indicative of operational status of the monitoring function of the sensor; and
a reporting function conveying the current grade to at least one device other than the sensor, and
wherein the data structure stores information pertaining to the sensor including at least priorities reflecting an expected: (i) robustness versus interferences of the sensor respective to the common physiological parameter and (ii) the current grade for the sensor;
wherein execution of the instructions stored in the memory of the sensor causes the sensor to perform a beaconing function outputting a beacon signal indicating a synchronization time, the beaconing function being performed only if information received from the second sensor indicates that the sensor is currently providing reliable information pertaining to the common physiological parameter having a highest quality relative to the quality of the information of the second sensor.

11. The apparatus of claim 10, wherein the common physiological parameter is selected from a group consisting of: heart rate; respiration; breathing rate; blood oxygenation; and core body temperature.

12. The apparatus of claim 10 wherein the sensor is one sensor of a plurality of sensors, each sensor of the plurality of sensors including a data structure configured to store information related to the corresponding sensor, a transceiver configured to send and receive data from the other sensors, a processor; and a memory configured to store machine-executable instructions, wherein execution of the instructions causes the sensors to each perform the monitoring function and the grading function;
wherein the data structure of each sensor stores information pertaining to the corresponding sensor including at least priorities of an expected: (i) accuracy and robustness versus interferences of the plurality of sensors respective to the common physiological parameter and (ii) the current grades for the sensors of the plurality of sensors;
wherein execution of the instructions stored in the memory of each sensor causes each sensor of the plurality of sensors to perform at least one output function generating an output signal conditional upon content of the data structure including at least the priorities and the current grades of the sensors of the plurality of sensors indicating the output function should be performed.

13. The apparatus as set forth in claim 12, wherein execution of the instructions stored in the memory of each sensor causes each sensor to independently perform an instance of a coordination function that selects an output sensor from the plurality of sensors, the coordination function including:
- controlling the corresponding wireless transceiver to transmit the current grade for the sensor to the other transceivers of the sensors of the plurality of sensors,
- controlling the corresponding wireless transceiver to receive the current grade for each other sensor of the plurality of sensors,
- constructing an instance of the data structure at each sensor, and
- selecting an output sensor from the plurality of sensors based on content of the data structure including at least the priorities and the current grades of the sensors of the plurality of sensors.

14. The apparatus of claim 10, wherein execution of the instructions stored in the memory of the sensor causes the sensor is to perform an alarm function outputting an alarm responsive to an alarm condition wherein the alarm condition requires that at least the following conditions are met:
   (i) sensor data acquired by the monitoring function of the sensor indicates an abnormal value for the common physiological parameter, and
   (ii) information received from a second sensor that indicates that no sensor is showing a normal reading for the common physiological parameter;
   wherein the alarm is audibly with an audible alarm or visually output with a flashing light.

15. The apparatus of claim 14, wherein execution of the instructions stored in the memory of the sensor causes the sensor perform an instance of a coordination function including receiving the current grade or current grades for the second sensor, and condition (ii) comprises:
   (ii) the current grade or current grades for the second sensor together with the current grade for the sensor and a prioritization of the sensor and the second sensor indicates that the sensor is currently providing the most information pertaining to the common physiological parameter having a highest quality relative to the quality of the information of the second sensor.

16. An apparatus comprising:
a plurality of sensors, each sensor of the plurality of sensors operating independently of the other sensor or sensors of the plurality of sensors, each of the sensors including a data structure configured to store information related to the corresponding sensor, a transceiver configured to send and receive data from the other sensors of the plurality of sensors, a processor; and a memory configured to store machine-executable instructions, wherein execution of the instructions causes each sensor to perform at least:
   acquiring sensor data indicative of a common physiological parameter, and
   occasionally assigning a current grade for the sensor at a predetermined time pattern wherein the current grade is indicative of operational status of the monitoring function of the sensor; and
wherein each data structure stores information pertaining to the corresponding sensor including at least priorities reflecting an expected robustness versus interferences of the plurality of sensors respective to the common physiological parameter and the current grades for the sensors of the plurality of sensors;
execution of the instructions stored in the memory of each sensors causes each sensor of the plurality of sensors to perform independently perform an instance of outputting at least one of:
   (1) an alarm responsive to an alarm condition wherein the alarm condition requires that at least the following conditions are met:
      (i) sensor data acquired by the monitoring function of a selected sensor indicates an abnormal value for the common physiological parameter, and
      (ii) information received from a medical monitor in wireless communication via one or more access points with the selected sensor, the received information indicating that no sensor is showing a normal reading for the common physiological parameter; and
   (2) a beacon signal indicating a synchronization time, the beaconing function being performed only if information received from the medical monitor indicates that the corresponding sensor is currently providing the information pertaining to the common physiological parameter having a highest quality relative to the quality of the information of the other sensors;
wherein the alarm is audibly with an audible alarm or visually output with a flashing light;
wherein execution of the instructions stored in the memory of the sensor causes the sensor to perform a beaconing function outputting a beacon signal indicating a synchronization time, the beaconing function being performed only if information received from the second sensor indicates that the sensor is currently providing reliable information pertaining to the common physiological parameter having a highest quality relative to the quality of the information of the second sensor.

17. The apparatus of claim 16, wherein at least one of:
the condition (ii) comprises (ii) information received from the medical monitor indicates that the selected sensor is selected as an output sensor; and
wherein execution of the instructions stored in the memory of the selected sensor causes the selected sensor to perform an instance of a coordination function including receiving the current grade or current grades for the at least one sensor other than the selected sensor, and condition (ii) comprises (ii) the current grade or current grades for the at least one sensor other than the selected sensor together with the current grade for the selected sensor and a prioritization of the selected sensor and the at least one sensor other than the selected sensor indicates that the selected sensor is currently providing the most reliable information pertaining to the common physiological parameter.

* * * * *